United States Patent
Reid, Jr. et al.

(10) Patent No.: US 7,434,423 B1
(45) Date of Patent: Oct. 14, 2008

(54) IMPACT PROTECTION AND PERFORMANCE GARMENT

(75) Inventors: Lawrence G. Reid, Jr., Germanton, NC (US); Darrell Gray Dollyhite, Rural Hall, NC (US)

(73) Assignee: Carolon Company, Rural Hall, NC (US)

( * ) Notice: Subject to any disclaimer, the term of this patent is extended or adjusted under 35 U.S.C. 154(b) by 659 days.

(21) Appl. No.: 11/118,041

(22) Filed: Apr. 29, 2005

Related U.S. Application Data

(60) Provisional application No. 60/566,958, filed on Apr. 30, 2004.

(51) Int. Cl.
*D04B 1/26* (2006.01)
(52) U.S. Cl. .................................................. 66/178 A
(58) Field of Classification Search ............... 66/178 A, 66/178 R, 183, 172 E; 2/239, 240, 241, 242; 602/63, 62
See application file for complete search history.

(56) References Cited

U.S. PATENT DOCUMENTS

| | | | |
|---|---|---|---|
| 858,006 A | 6/1907 | Lum | |
| 1,257,643 A | 2/1918 | Smith | |
| 1,890,299 A * | 12/1932 | Mutchler et al. | 66/178 A |
| 3,856,008 A | 12/1974 | Fowler et al. | |
| 4,172,456 A * | 10/1979 | Zens | 602/63 |
| 4,180,065 A * | 12/1979 | Bowen | 602/63 |
| 4,253,317 A * | 3/1981 | Howard et al. | 66/186 |
| 4,397,161 A * | 8/1983 | Chesebro et al. | 66/178 A |
| 4,502,301 A | 3/1985 | Swallow et al. | |
| 4,513,740 A | 4/1985 | Westlake | |
| 5,653,128 A | 8/1997 | Warren, Jr. et al. | |
| 6,012,177 A * | 1/2000 | Cortinovis | 2/239 |
| 6,173,452 B1 * | 1/2001 | Kelly et al. | 2/240 |
| 6,430,970 B1 * | 8/2002 | Gardon-Mollard et al. | 66/178 A |
| 6,613,007 B1 | 9/2003 | Reid, Jr. | |
| 6,755,052 B1 * | 6/2004 | Sytz | 66/196 |

FOREIGN PATENT DOCUMENTS

FR        2432867       7/1980

* cited by examiner

*Primary Examiner*—Danny Worrell
(74) *Attorney, Agent, or Firm*—Kilpatrick Stockton LLP

(57) ABSTRACT

A tubular garment includes a number of zones of compressive pressure about the circumference of the garment. A zone of compressive pressure in the distal portion of the garment includes a stitch pattern that is more dense than at least a portion of the stitch pattern in a zone of compressive pressure in the proximal portion of the garment. As a result, the compressive pressure in the distal portion zone is greater than the compressive pressure in the proximal portion zone. A more dense stitch pattern in one portion of a single zone can provide cushioning and increased compressive pressure compared to another portion of the zone. A more dense stitch pattern useful in such garments includes tuck stitches.

21 Claims, 7 Drawing Sheets

IMPACT PROTECTION AND PERFORMANCE GARMENT

CROSS-REFERENCE TO RELATED APPLICATION

This application claims priority to, and incorporates herein in-full by reference, Applicant's co-pending provisional patent application having U.S. Ser. No. 60/566,958, filed Apr. 30, 2004.

FIELD OF THE INVENTION

The present invention relates to garments and, in particular, to hosiery garments comprising increased compressive pressure and cushioning in selected areas of the garments. Embodiments of the present invention provide a knit construction that can increase compressive pressure to selected parts of the anatomy of a wearer.

BACKGROUND OF THE INVENTION

Many people involved in physical activity can experience injury and fatigue in the lower leg and feet. Developing a device that reduces the impact of stress from such activity, including the risk of trauma related to absorbing the impact of activity, and that promotes circulation in the lower extremities will not only reduce the chance of injury but improve performance.

Conventional socks, such as athletic socks, include, for example, a terry stitch in attempt to absorb the impact of physical stress. While such sock constructions can absorb some energy from impact, such heavier constructions do not provide optimal shock absorbing characteristics.

Thus, there is a need to provide a tubular garment, such as a sock, having a construction that provides improved shock absorbing characteristics. There is a need to provide a sock that improves circulation through compression in combination with improved shock absorbing properties. There is also a need for a sock having such characteristics that provides a contoured fit and that has smooth transitions from one area of compressive pressure to another. Such a sock would provide a means for promoting circulation and reducing impact stress in selected areas of a wearer's foot and/or leg.

SUMMARY OF THE INVENTION

The present invention provides embodiments of a garment that includes a means for providing increased compressive pressure in selected areas of the garment to a wearer. In an embodiment, such a garment can include both a means for providing increased compressive pressure in selected areas of the garment and a means for improved shock absorption in selected areas. For example, embodiments of a sock according to the present invention can include a means for providing increased compressive pressure in selected areas of the sock, such as the arch, heel, ankle, and/or calf areas, and a means for improved shock absorption in one or more of those areas. In embodiments, the means for providing increased compressive pressure and the means for improved shock absorption can comprise a dense stitch pattern that includes, for example, tuck stitches.

In embodiments, such a garment can include a densely-knit stitch pattern comprising tuck stitches and a decreased knitting circumference to provide increased compressive pressure in selected areas. In other embodiments, such a garment can include a densely-knit stitch pattern comprising tuck stitches and an elastomeric yarn to provide increased compressive pressure in selected areas.

In one illustrative embodiment, a tubular garment can comprise a plurality of zones of compressive pressure about a circumference of the garment. A first zone of compressive pressure can be located in the distal portion of the garment, and a second zone of compressive pressure can be located in the proximal portion of the garment. The first zone comprises a first stitch pattern that provides a first compressive pressure, and the second zone comprises a second stitch pattern that provides a second compressive pressure. The first stitch pattern is more dense than at least a portion of the second stitch pattern. As a result, the first compressive pressure (in the distal portion) is greater than the second compressive pressure (in the proximal portion).

In another illustrative embodiment, a garment can include a zone of compressive pressure that comprises a first portion of the garment circumference and a second portion of the same garment circumference. The stitch pattern of the first portion is more dense than the second portion stitch pattern, such that the first portion compressive pressure is greater than the second portion compressive pressure. In this manner, increased compressive pressure can be provided to selected areas in the garment.

Features of an impact protection and performance garment of the present invention may be accomplished singularly, or in combination, in one or more of the embodiments of the present invention. As will be appreciated by those of ordinary skill in the art, the present invention has wide utility in a number of applications as illustrated by the variety of features and advantages discussed below.

Embodiments of an impact protection and performance garment of the present invention provides numerous advantages over prior tubular garments. For example, the present invention can advantageously provide a garment that includes an increased amount of compressive pressure in selected areas of the foot and/or leg portions of the garment so as to promote circulation.

Another advantage is that the present invention can provide a garment that includes enhanced cushioning and shock absorbing characteristics to selected areas of the foot and/or leg portions of the garment so as to decrease frictional stress to those areas.

Another advantage is that the present invention can provide a garment that includes a shock absorbing effect in selected areas of the foot and/or leg portions without adding additional fabric, such as in a two-ply sock, or a substantial thickness such as in a terry layer.

Another advantage is that the present invention can provide a garment that combines both an increased amount of compressive pressure and a shock absorbing effect in selected areas of the foot and/or leg portions of the garment using the same technique.

Another advantage is that the present invention can provide a garment comprising pre-determined amounts of compressive pressure in selected areas of the garment. Such embodiments provide a therapeutic compression garment having selected zones of therapeutic compressive pressures to enhance flow in the venous and lymphatic systems.

Another advantage is that the present invention can provide a garment that can exhibit such improved characteristics using particular combinations of common stitch patterns.

As will be realized by those of skill in the art, many different embodiments of an impact protection and performance garment according to the present invention are possible. Additional uses, objects, advantages, and novel features of the invention are set forth in the detailed description that follows and will become more apparent to those skilled in the art upon examination of the following or by practice of the invention.

DETAILED DESCRIPTION

Figure 1:
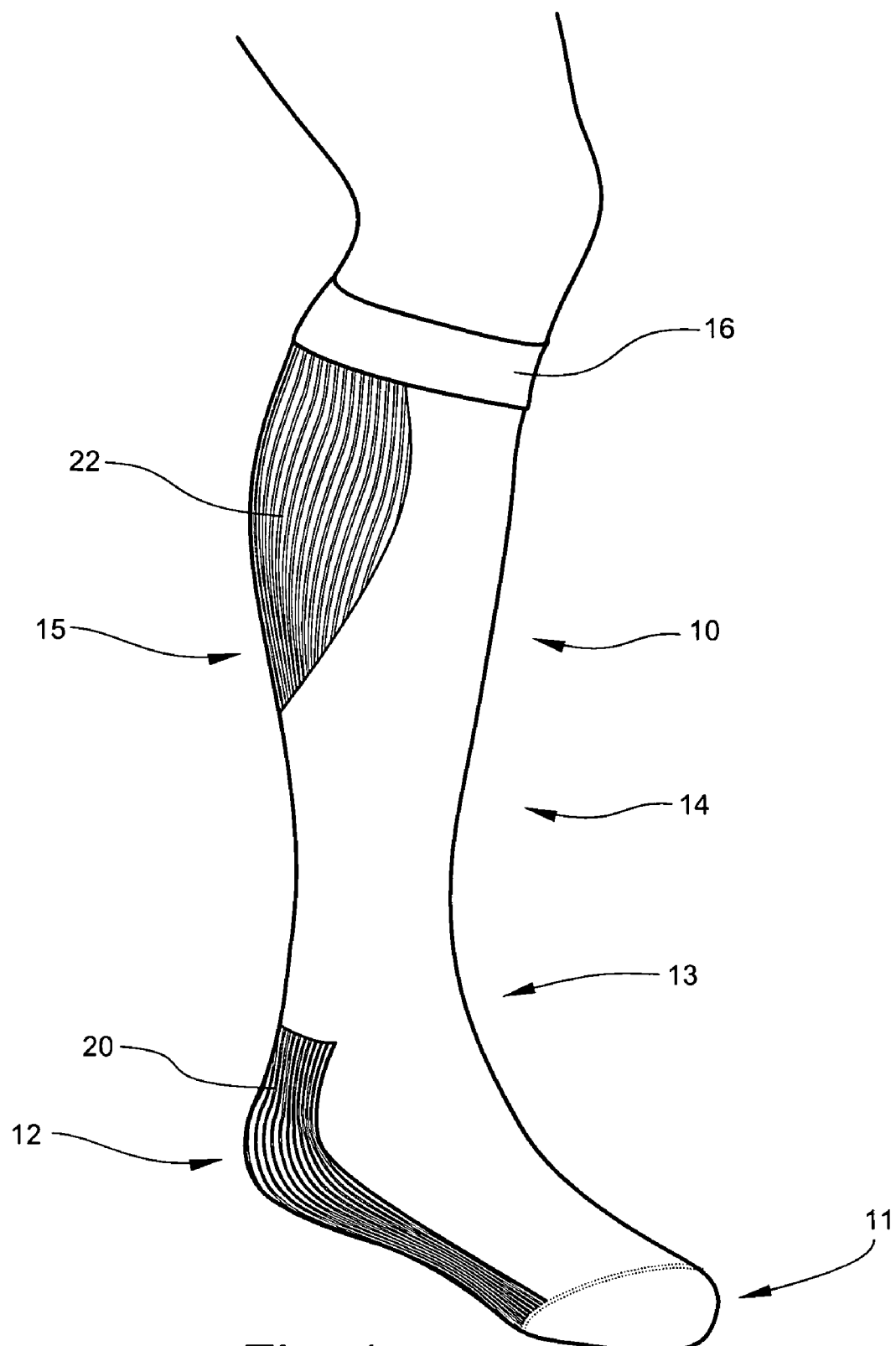
FIG. 1 is a perspective view of a knee-high sock having zones of a more densely knit stitch pattern in the heel and calf areas providing increased compressive pressure in those areas in an embodiment of the present invention.

The present invention provides embodiments of a garment that includes a means for providing increased compressive pressure in selected areas of the garment to a wearer. In an embodiment, such a garment can include both a means for providing increased compressive pressure in selected areas of the garment and a means for improved shock absorption in selected areas. For example, embodiments of a sock according to the present invention can include a means for providing increased compressive pressure in selected areas of the sock, such as the arch, heel, ankle, and/or calf areas, and a means for improved shock absorption in one or more of those areas.

In embodiments, the means for providing increased compressive pressure and the means for improved shock absorption can comprise a dense stitch pattern that includes, for example, tuck stitches. In embodiments, garments may include portions having a more tightly knit stitch pattern such that the resulting increased compressive pressure is graduated along the length of the garment. FIGS. 1-12 show such embodiments.

In embodiments, such a garment can include a densely-knit stitch pattern comprising tuck stitches and a decreased knitting circumference to provide increased compressive pressure in selected areas. In other embodiments, such a garment can include a densely-knit stitch pattern comprising tuck stitches and an elastomeric yarn to provide increased compressive pressure in selected areas.

Embodiments including such construction would provide comfort to a wearer in areas having a high coefficient of friction. For example, addition of a cushioning construction to the heel and the bottom portion of the foot decreases frictional stress to both the heel and foot of a wearer.

Knitting machines can be programmed to form many different stitch types by manipulating the movement of the knitting needles to pick up yarn, form a stitch, and then remove, or shed, the yarn. Various forms of jersey, rib, or alternate stitches are standard in the industry. A jersey stitch is defined as a plain, single-knit stitch that produces a flat fabric surface. (Fairchild's Dictionary of Textiles, 7$^{th}$ Edition, p. 224.) A rib stitch is defined as a knitting stitch characterized by alternation of wales on the two sides of the fabric. Two rows of needles are employed, one knitting the wales of the face, and the other knitting the back wales. (Fairchild's Dictionary of Textiles, 7$^{th}$ Edition, p. 472.)

A tuck stitch, or a tuck height stitch, is defined as a knitting stitch that produces tuck or openwork effects by having certain needles hold more than one stitch at a time. (Fairchild's Dictionary of Textiles, 7$^{th}$ Edition, p. 591.) In a tuck stitch, the needles in the upper knitting position do not knit, but an extra loop of yarn is laid over the needles. The extra loop is not intermeshed through the old loop but is tucked in behind it on the reverse side of the stitch. When these needles are returned to a knitting position, all the loops on the needle are knit in a single stitch, resulting in a textured fabric. (David J. Spencer, Knitting Technology, p. 59). The yarn of a tuck stitch that lies on top of the previous loop makes fabric thicker and shorter in length. A series of tuck stitches provides a stitch pattern that is more dense than plain jersey stitches or rib stitches. A more dense tuck stitch pattern can provide cushioning to a wearer of a garment having such a pattern.

Circular knitting machines are used in the knitting industry to knit various fabrics. Embodiments of garments according to the present invention can be made on a conventional circular knitting machine. In order to knit a fabric utilizing a circular knitting machine, a plurality of ends of yarn are supplied to a plurality of needles cylindrically disposed around the cylinder of the circular knitting machine. A plurality of stitch cams disposed around the cylinder define the travel path of the needles. The needles demand a certain quantity of yarn per revolution of the knitting machine when the machine is operating according to the stitch cam settings of the knitting machine.

A densely knit stitch construction pattern in embodiments of the present invention can be accomplished by knitting on a fine gauge, multi-feed, circular knitting machine. When knitting, specific needles are manipulated to various heights and are combined with specific yarn feeds.

Stitch density is defined as the total number of loops in a measured area of fabric. It is the total number of needle loops in a given area, for example, a square inch or three square centimeters. Stitch density is determined by counting the number of courses in one inch (or three cms) and the number of wales in one inch (or three cms), then multiplying the number of courses by the number of wales. (David J. Spencer, Knitting Technology, p. 17.)

The density of a stitch can be manipulated by the selection of various yarns. The amount of yarn that is fed to the needles of a circular knitting machine also helps determine the density of the fabric being knitted. For example, if it is desired to knit a denser fabric, the amount of yarn fed to the needles per revolution of the knitting machine is decreased, thereby increasing yarn tension, and making smaller stitches. If it is desired to knit a less dense fabric, the amount of yarn fed to the needles per revolution of the knitting machine is increased, thereby decreasing yarn tension, and increasing the size of the stitches. Thus, in order to control the density of a fabric, it is desirable to control the rate at which yarn is fed to a circular knitting machine.

The number of yarn feeds in a circular knitting machine refers to the number of yarns fed into a knitting machine cylinder at each revolution as it knits continuous rows of stitches. The number of yarn feeds can be expressed per inch of the cylinder diameter. For example, a four-feed machine would have four feeds of yarn per inch of the cylinder diameter. (Fairchild's Dictionary of Textiles, 7$^{th}$ Edition, p. 213.) Reference herein to a particular "feed" refers to the specific yarn provided by that yarn feed.

In embodiments of the present invention, a more densely knit stitch pattern comprises an "impact stitch" or a "modified impact stitch" pattern. An "impact stitch" is defined as a stitch pattern in which each stitch in at least one yarn feed in a pattern comprises a tuck stitch. The "impact stitch" provides an increased amount of compressive pressure in the circumference of a tubular garment. The "impact stitch" provides an increased amount of cushioning in a garment. Thus, in embodiments of the present invention, an "impact stitch" can provide both increased cushioning and increased compressive pressure by a garment to an anatomical area of a wearer underlying a portion of the garment incorporating the "impact stitch." A "modified impact stitch" is defined as a stitch pattern in which at least one, but less than all, stitches in a yarn feed pattern comprises a tuck stitch. The "modified impact stitch" provides an amount of increased compressive pressure but less than the amount of increase in compressive pressure provided by the unmodified "impact stitch."

In the "impact stitch," after the needles have picked up the yarn, formed a stitch, and moved to the next feed where the yarn is normally shed from the needles, the needle is instead brought up just high enough for the needles to take on yarn (tuck height) but not high enough to shed the yarn, or stitch. Then, on the next feed, the needles are brought to sufficient height to clear the yarn.

In embodiments, the "impact stitch" of the present invention may provide an increase in compressive pressure in a horizontal direction about a tubular garment circumference. For example, in a sock 10, 50 having a stitch pattern in a portion of the calf area 15 in which each stitch in the fourth yarn feed comprises a tuck stitch (the "impact stitch"), the compressive pressure in the calf area 15 was measured at 22-23 mm Hg. In the same sock 10, 50 without the "impact stitch" in the calf area 15, the compressive pressure was measured at 17 mm Hg. Thus, it was discovered that the "impact stitch" can provide an increase in compressive pressure, for example, from about a 5% increase to as much as a 50% increase or more, depending on the particular yarns used and the number of tuck stitches in the garment circumference.

Compressive pressures of tubular garments 10, 30, 50 according to the present invention can be measured using commercially available equipment for this purpose. Compressive pressures of tubular garments are generally measured at a particular anatomical level about the entire circumference of the garments. Increased compressive pressure measured about a wearer's leg in the calf area, for example, can be sufficient to provide a perceptible difference in compressive pressure to the wearer as compared to that provided by a sock or tight having the same size and yarn(s) but with a less densely knit stitch pattern in the calf portion.

The amount of increase in compressive pressure provided in embodiments of the present invention can vary depending on the intended use of the garment 10, 30, 50 and the degree of additional support desired in a particular anatomical area. For example, an embodiment of a sock 10, 50 designed to be worn by a worker standing for long periods at a work station may include a more tightly knit stitch in the ball 51, arch 52, and heel 53 portions of the sock 50 shown in FIG. 3. This knit configuration would provide both cushioning support and increased compressive pressure support to a wearer's foot, thereby decreasing the stress from prolonged standing.

Figure 2:
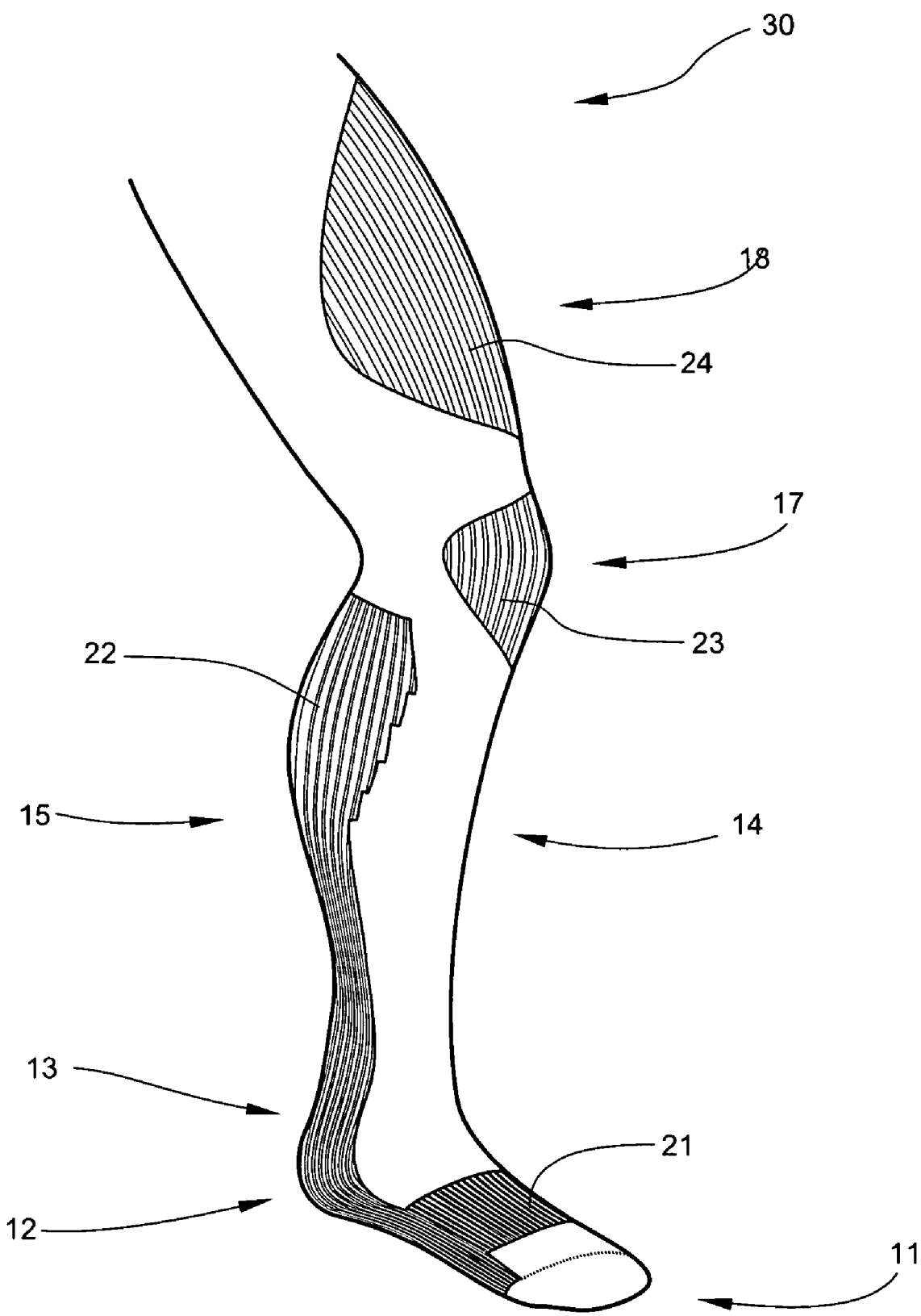
FIG. 2 is a perspective view of one leg of a tight having zones of a more densely knit stitch pattern in the heel, calf, knee, and anterior thigh areas providing increased compressive pressure in those areas in an embodiment of the present invention.

In another embodiment, a thigh-high "legging," for example as shown in FIG. 2, designed to be worn during activities involving more movement, such as walking and sports activities, a more tightly knit stitch can be included in the heel 12 and foot portions and in the ankle 13, calf 15, and knee 17 portions of the legging 30. This knit configuration would provide both cushioning support and increased compressive pressure support to not only the foot but also the ankle 13, calf 15, and knee 17 areas that may receive increased stress from movements typical in such activities.

Embodiments of garments 10, 30, 50 according to the present invention may have actual compressive pressures in use that vary from the compressive pressures measured during manufacture of the garments 10, 30, 50. During manufacture, compressive pressures are measured against a tubular form having a particular circumference. Such variations can be due, at least in part, to variations in the anatomy of wearers. Compressive pressures can be increased or decreased relative to a pressure of the garment 10, 30, 50 measured during manufacture because the size and/or shape of an underlying structure, such as an ankle, varies from the standard-sized measuring form. Moreover, compressive pressures generated by the same garment 10, 30, 50 may vary between wearers because of such variations in the anatomy of wearers.

Figure 3:
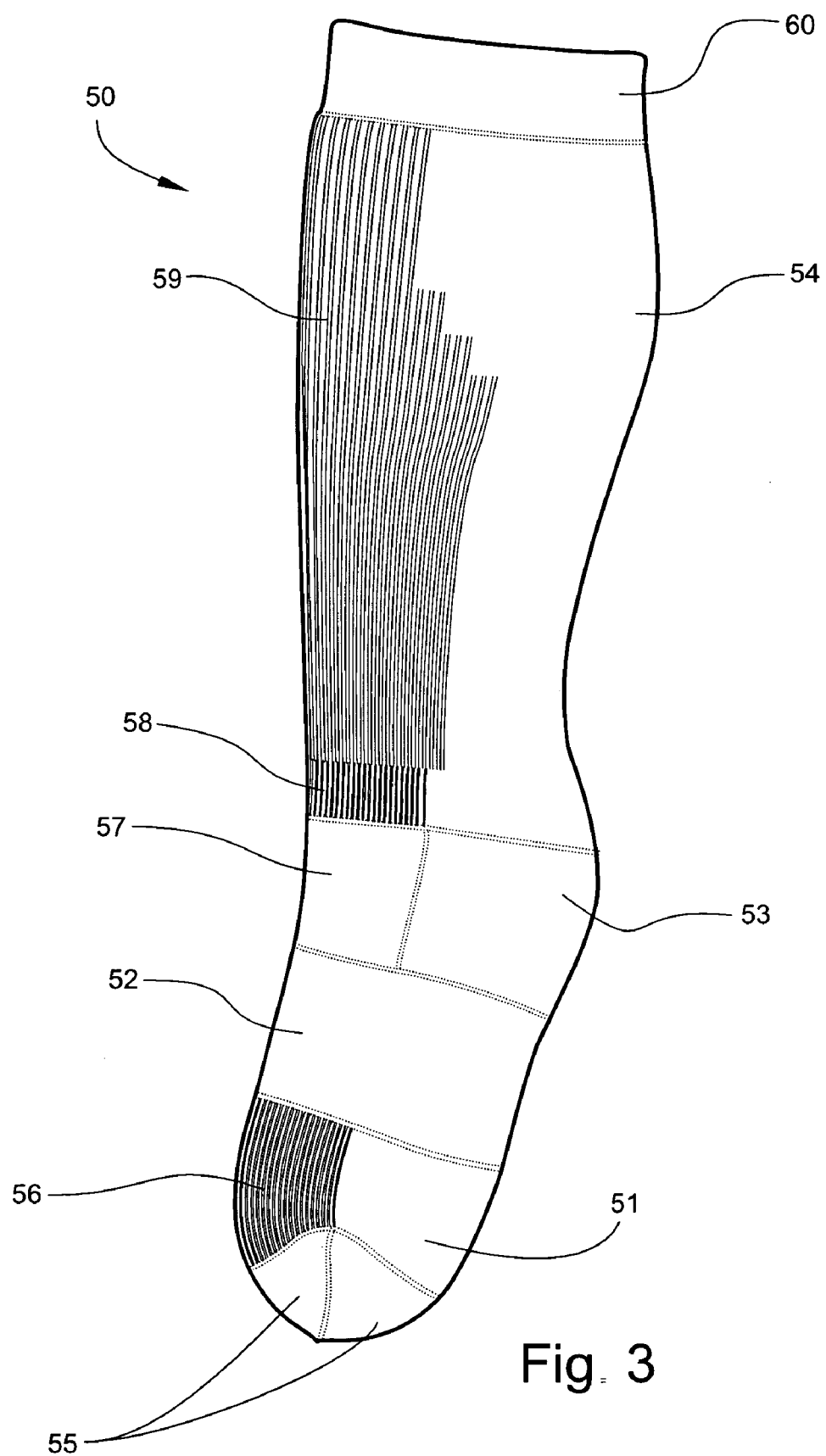
FIG. 3 is a side view of a knee-high sock having a plurality of zones of a more densely knit stitch pattern providing increased compressive pressure in those zones and graduated compressive pressure from the distal portion to the proximal portion of the sock in an embodiment of the present invention.

In embodiments of the present invention, a densely knit "impact stitch" 51-54, as shown in FIG. 3, comprising tuck stitches in selected areas of a tubular garment 10, 30, 50 can be combined with other cushion-providing stitch patterns in other parts of the garment 10, 30, 50. For example, a garment 10 (FIG. 1) according to the present invention may include an "impact stitch," in which each stitch in a fourth yarn feed pattern comprises a tuck stitch, in a portion of the calf area 15, and the bottom, or sole, of the garment 10 may include a terry stitch for cushioning in the bottom of the garment 10. In such an embodiment, shock absorption could be improved in both the calf 15 and foot areas and circulation could be enhanced in the calf area. The impact stitch can be used in conjunction with other standard stitches to produce desired effects in fabric.

The "impact stitch" may provide a heavier hand similar to that provided by the looped face of a knitted terry fabric. Such a hand can provide a more comfortable feel to a wearer than the fabric in a tubular garment having the same compressive pressure but with a less densely knit stitch pattern. Yet, the "impact stitch" provides a comfortable feel with excessively increasing the thickness of the garment.

In the embodiment shown in FIG. 1, a garment 10 is a knee-high sock having zones of a more densely knit stitch pattern in the heel 12 and calf areas 15 as compared to the toe 11, ankle 13, shin 14, and welt 16 areas. For example, the heel stitch pattern 20 and the calf stitch pattern 22 can each comprise an "impact stitch," in which each stitch in a fourth yarn feed pattern comprises a tuck stitch, as described above. Thus, in sock 10, the circumferences, or zones of compression, in the heel 12 and calf 15 areas can provide increased compressive pressure in those zones as compared to the toe 11, ankle 13, shin 14, and welt 16 areas.

In the embodiment shown in FIG. 2, a garment 30 is a tight having zones of a more densely knit stitch pattern in the arch 21, heel 12, ankle 13, calf 15, knee 17, and anterior thigh 18 areas as compared to the toe 11 and shin 14 areas. The arch stitch pattern 21, calf stitch pattern 22, the knee stitch pattern 23, and the thigh stitch pattern 24 each comprise an "impact stitch" including tuck stitches. Thus, in tight 30, the circumferences, or zones of compression, in the heel 12, ankle 13, calf 15, knee 17, and anterior thigh 18 areas can provide increased compressive pressure in those zones as compared to the toe 11 and shin 14 areas. In another embodiment, the knee stitch pattern 23 can encircle (not shown) a portion of the knee 17 to provide increased compressive pressure and cushioning about the perimeter of the knee cap.

As shown in the embodiments in FIGS. 1-2, the distal portion of the garments 10, 30, respectively, comprises the lower part of the garment away from the center of a wearer's body, such as the toe 11 and/or the heel 12. The proximal portion of the garments 10, 30, comprise the area of the garment 10, 30, closer to the center of a wearer's body, for example, the area comprising the calf 15 in the embodiment shown in FIG. 1, and the calf 15 and/or the thigh 18 in the embodiment in FIG. 2.

In the illustrative embodiment shown in FIG. 3, a knee-high sock 50 includes a plurality of zones of a more densely knit stitch pattern providing increased compressive pressure in those zones. The zones of compressive pressure are graduated from the distal portion (toe and arch area) to the proximal portion (calf and welt area) of the sock 50. The sock 50 includes seven zones of compression around the circumference of the sock 50. Within these seven zones, ten areas comprise a particular stitch pattern 51-60. Four of the areas comprise the same stitch pattern 51-54, designated as an "impact stitch," in which each stitch in a fourth yarn feed pattern comprises a tuck stitch, as described above. Four other areas comprise stitch patterns 56-59 that include a "modified impact stitch," in which at least one, but less than all, stitches in a fourth yarn feed pattern comprises a tuck stitch. The "modified impact stitch" provides an amount of increased compressive pressure but less than the amount of increase in compressive pressure provided by the unmodified "impact stitch."

Figure 6:
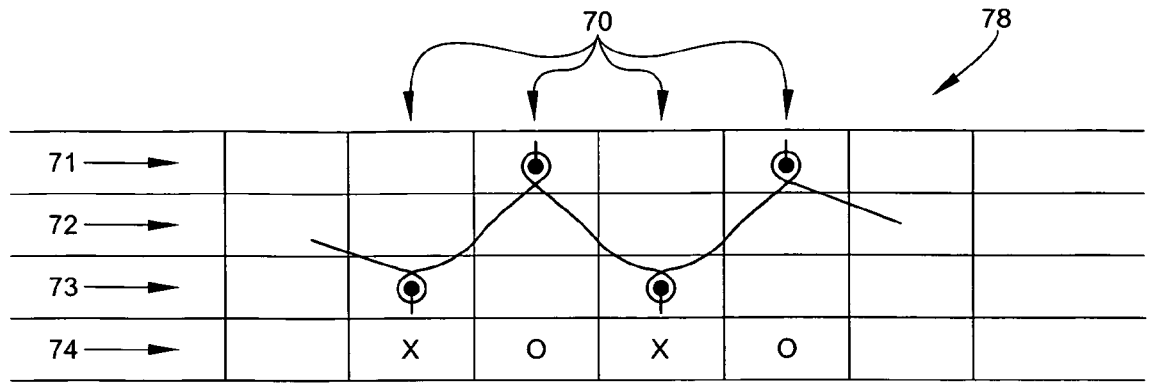
FIG. 6 is a knitting notation for a 1×1 alternate rib stitch in an embodiment of the present invention.
Figure 7A:
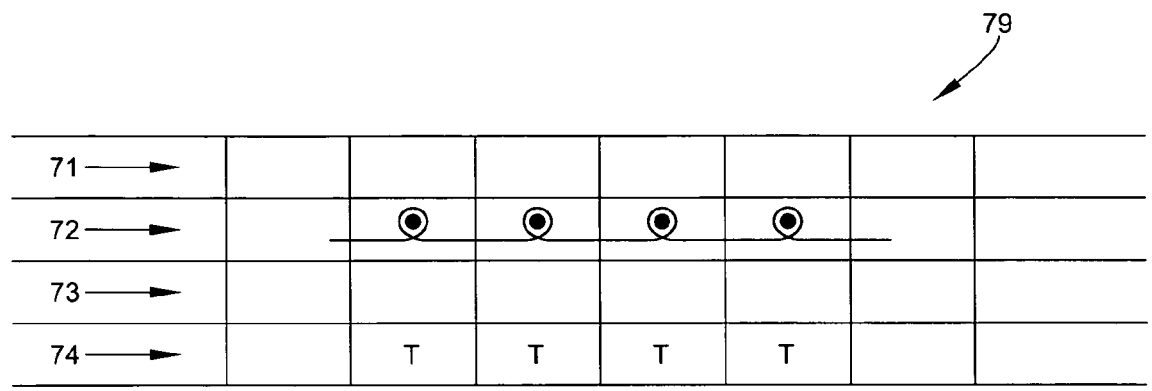
FIG. 7A is a knitting notation for a tuck stitch on all four needles produced by needles in the "up" knitting position in an embodiment of the present invention.
Figure 7B:
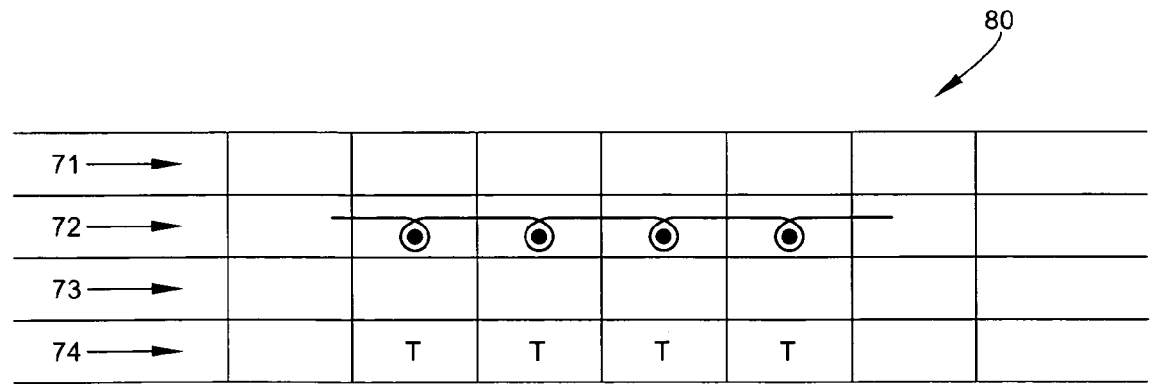
FIG. 7B is a knitting notation for a tuck stitch on all four needles produced by needles in the "down" knitting position in an embodiment of the present invention.

In the embodiment shown in FIG. 3, the interior distal foot stitch pattern 51, the arch stitch pattern 52, the heel stitch pattern 53, and the calf stitch pattern 54 each comprise the following stitch pattern: first feed—1×1 rib stitch (FIG. 5); second feed—jersey stitch (FIGS. 4A and 4B); third feed—1×1 alternate rib stitch (FIG. 6); and fourth feed—all tuck stitches (FIGS. 7A and 7B).

The toe stitch pattern 55 comprises a jersey stitch (FIGS. 4A and 4B) on all four feeds.

Figure 10:
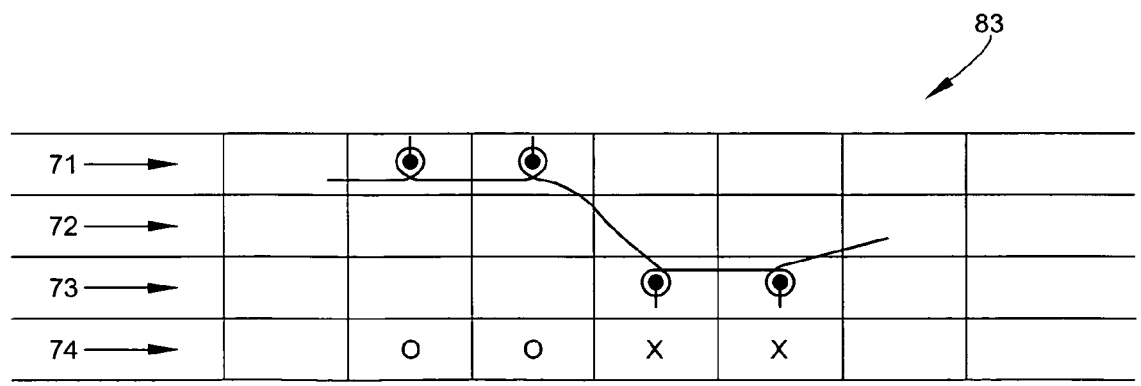
FIG. 10 is a knitting notation for a 2×2 rib stitch in an embodiment of the present invention.
Figure 11:
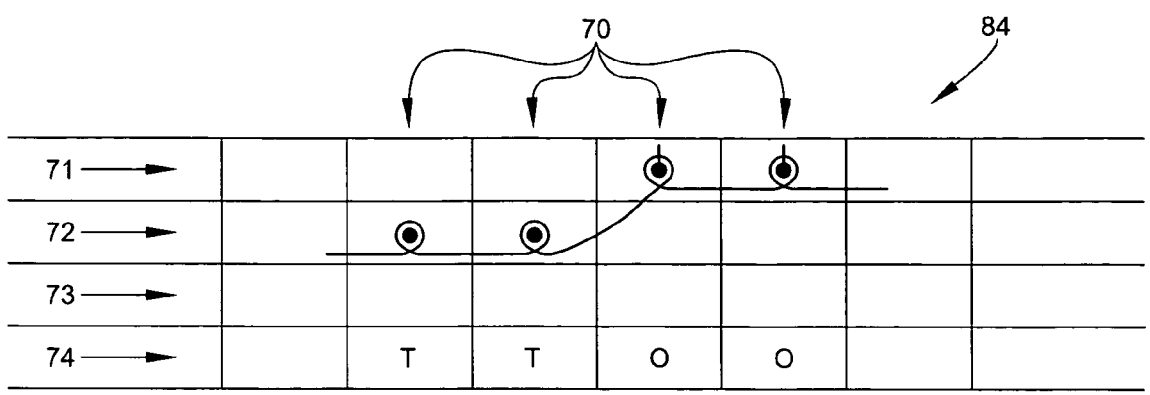
FIG. 11 is a knitting notation for a 2×2 alternate rib stitch with a 2×2 tuck stitch alternating with the 2×2 alternate rib stitch in an embodiment of the present invention.

The superior distal foot stitch pattern 56 comprises the following stitch pattern: first feed—2×2 rib stitch (FIG. 10); second feed—jersey stitch (FIGS. 4A and 4B); third feed—2×2 rib stitch (FIG. 10); and fourth feed—a 2×2 alternate rib stitch with tuck stitches alternating with the 2×2 alternate rib stitch (FIG. 11).

Figure 12:
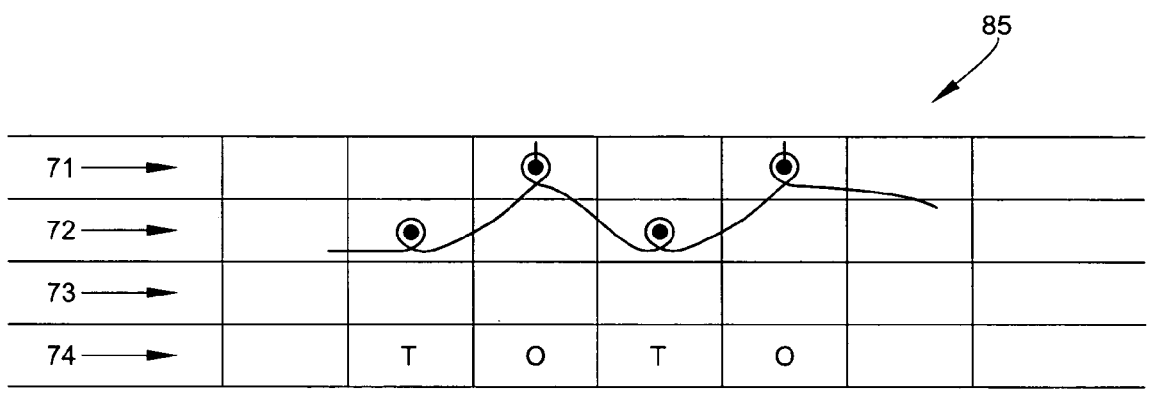
FIG. 12 is a knitting notation for a 1×1 alternate rib stitch with a 1×1 tuck stitch alternating with the 1×1 alternate rib stitch in an embodiment of the present invention.

The superior heel stitch pattern 57 comprises the following stitch pattern: first feed—1×1 rib stitch (FIG. 5); second feed—no stitch; third feed—1×1 rib stitch (FIG. 5); fourth feed—1×1 alternate rib stitch with a 1×1 tuck stitch alternating with the 1×1 rib stitch (FIG. 12).

The anterior ankle stitch pattern 58 comprises the superior distal foot stitch pattern 56 described above.

Figure 8:
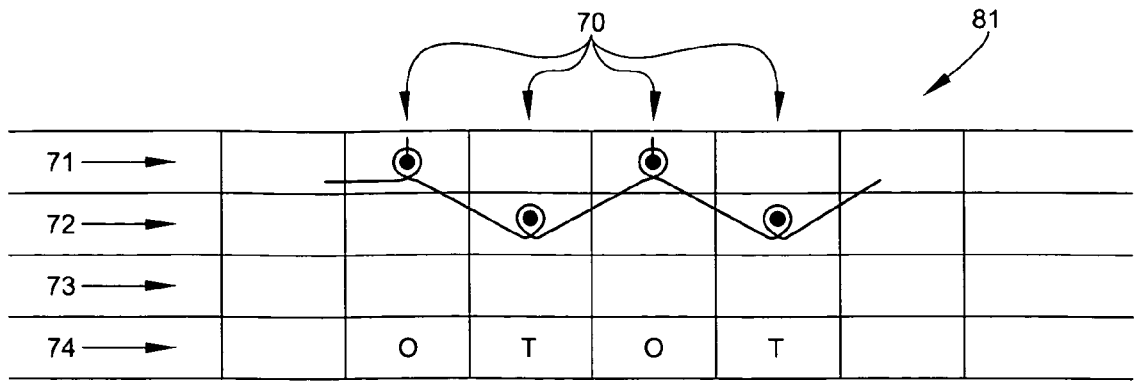
FIG. 8 is a knitting notation for a 1×1 rib stitch with a 1×1 tuck stitch alternating with the 1×1 rib stitch in an embodiment of the present invention.

The shin stitch pattern 59 comprises the following stitch pattern: first feed—3×1-1×1 rib stitch (FIG. 9); second feed—jersey stitch (FIGS. 4A and 4B); third feed—3×1-1×1 rib stitch (FIG. 9); and fourth feed—1×1 rib stitch with a 1×1 tuck stitch alternating with the 1×1 rib stitch (FIG. 8).

Figure 4A:
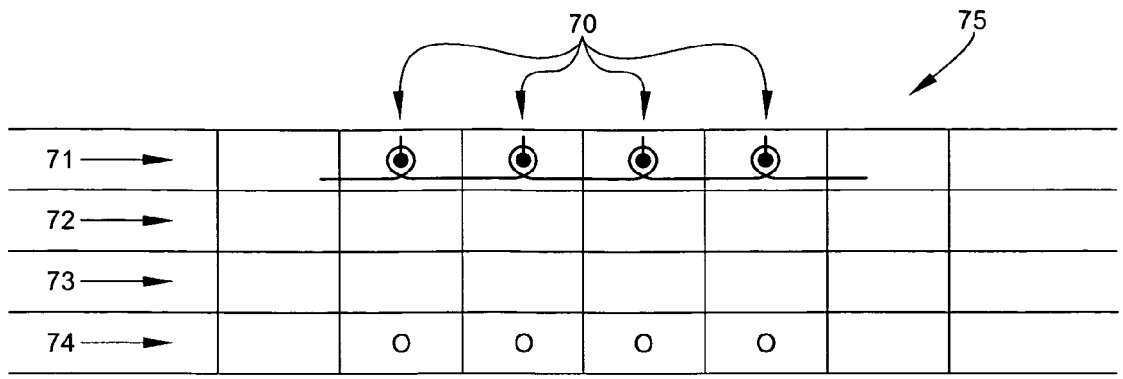
FIG. 4A is a knitting notation for a single jersey stitch produced by needles in the "up" knitting position in an embodiment of the present invention.
Figure 4B:
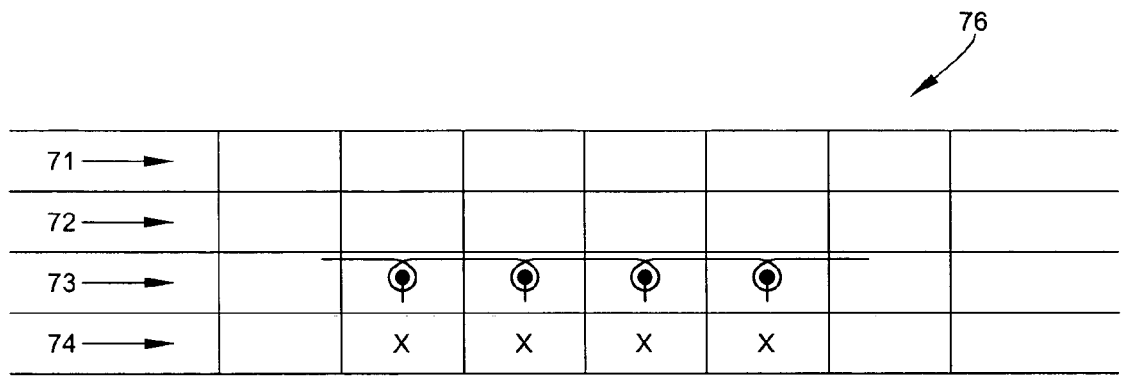
FIG. 4B is a knitting notation for a single jersey stitch produced by needles in the "down" knitting position in an embodiment of the present invention.

The welt stitch pattern 60 comprises the following stitch pattern: first feed—jersey stitch (FIGS. 4A and 4B); second feed—jersey stitch (FIGS. 4A and 4B); third feed—1×1 rib stitch (FIG. 5); and fourth feed—jersey stitch (FIGS. 4A and 4B).

As shown in FIG. 3, the arch stitch pattern 52 encircles the entire circumference of the sock in the arch area. As noted, the arch stitch pattern 52 comprises the "impact stitch," in which each stitch in a fourth yarn feed pattern comprises a tuck stitch. As a result, the arch stitch pattern 52 in the arch area of the sock 50 provides the greatest amount of increased compressive pressure of any of the zones of compression in the sock 50.

In the circumference adjacent and proximal to the arch area, the zone of compression comprises the heel stitch pattern 53 and the superior heel stitch pattern 57. The heel stitch pattern 53 comprises the "impact stitch," in which each stitch in a fourth yarn feed pattern comprises a tuck stitch, and the superior heel stitch pattern 57 comprises a modified "impact stitch" pattern, in which the fourth feed is a 1×1 alternate rib stitch with a 1×1 tuck stitch alternating with the 1×1 rib stitch. Thus, this zone of compression provides less compressive pressure than the arch area zone of compression.

In the circumference adjacent and proximal to the heel area, the ankle zone of compression comprises the calf stitch pattern 54 and the anterior ankle stitch pattern 58. The calf stitch pattern 54 comprises the "impact stitch," and the anterior ankle stitch pattern 58 comprises a modified "impact stitch" pattern, in which the fourth feed is a 2×2 alternate rib stitch with tuck stitches alternating with the 2×2 alternate rib stitch. The ankle zone of compression provides a lesser amount of compressive pressure than the adjacent distal heel zone of compression.

In the calf-shin circumference, the zone of compression comprises the calf stitch pattern 54 and the shin stitch pattern 59. The calf stitch pattern 54 comprises the "impact stitch," and the shin stitch pattern 59 comprises a modified "impact stitch" pattern, in which the fourth feed is a 1×1 rib stitch with a 1×1 tuck stitch alternating with the 1×1 rib stitch. The portion of the calf-shin zone of compression comprising the calf stitch pattern 54 varies along the contour of the calf area, such that the balance of "impact stitch" and "modified impact stitch" varies from a distal to a more proximal region in this zone of compression. As a result, the calf-shin zone of compression provides a gradually changing amount of compressive pressure along the length of the zone.

A knitting notation is defined as a symbolic representation of a knitted repeat sequence and its resultant fabric structure. In the knitting notation used herein (in FIGS. 4-12), each point in a box represents a knitting needle 70 in plan view from above, and the thread path represented by the curved lines represents the stitch. Each horizontal grouping of points thus represents adjacent needles during the same knitting cycle and the course produced by them. Needles represented by points in the lines 71 are in the "up" needle height position.

Needles represented by points in the lines 73 are in the "down" needle height position. Needles represented by points in the lines 72 are in the "tuck" needle height position. In the lines 74, an "X" is placed in a square where the stitch faces one direction. An "O" is placed in a square where the stitch faces the opposite direction from the "X" stitch. A "T" is placed in a square where the stitch is a "tuck" stitch.

Thus, the stitch patterns and knitting notations discussed with reference to FIG. 3, are shown in FIGS. 4-12, and described as follows. FIG. 4A is a knitting notation for a single jersey stitch 75 produced by needles in the "up" knitting position. FIG. 4B is a knitting notation for a single jersey stitch 76 produced by needles in the "down" knitting position.

Figure 5:
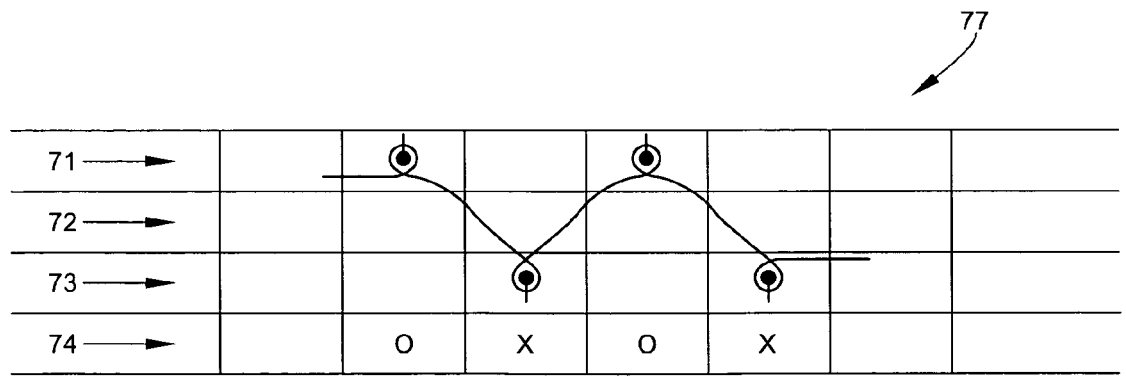
FIG. 5 is a knitting notation for a 1×1 rib stitch in an embodiment of the present invention.
Figure 9:
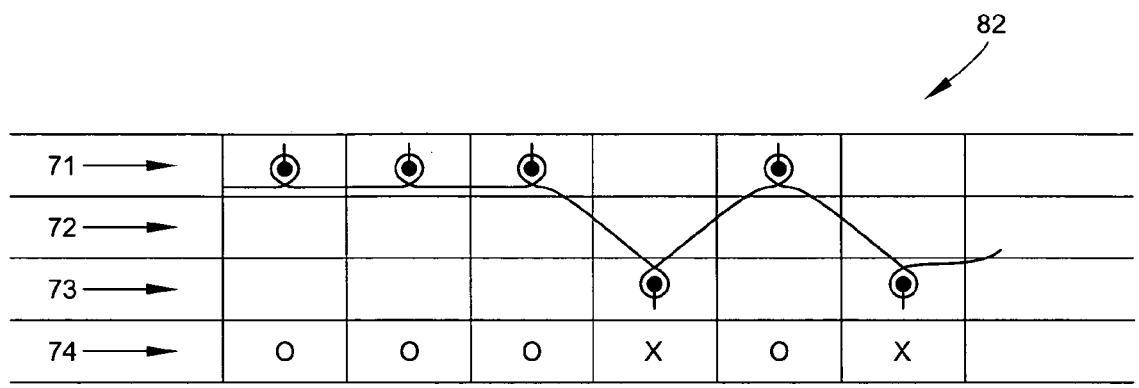
FIG. 9 is a knitting notation for a 3×1-1×1 rib stitch in an embodiment of the present invention.

FIG. 5 is a knitting notation for a 1×1 rib stitch 77. FIG. 6 is a knitting notation for a 1×1 alternate rib stitch 78. FIG. 7A is a knitting notation for a tuck stitch 79 on all four needles produced by needles in the "up" knitting position. FIG. 7B is a knitting notation for a tuck stitch 80 on all four needles produced by needles in the "down" knitting position. FIG. 8 is a knitting notation for a 1×1 rib stitch with a 1×1 tuck stitch alternating with the 1×1 rib stitch (81). FIG. 9 is a knitting notation for a 3×1-1×1 rib stitch 82. FIG. 10 is a knitting notation for a 2×2 rib stitch 83. FIG. 11 is a knitting notation for a 2×2 alternate rib stitch with a 2×2 tuck stitch alternating with the 2×2 alternate rib stitch (84). FIG. 12 is a knitting notation for a 1×1 alternate rib stitch with a 1×1 tuck stitch alternating with the 1×1 alternate rib stitch (85).

In embodiments in which a zone of compressive pressure surrounds the foot or leg portion of the garment 10, 30, 50, changes in compressive pressure from one area of the garment 10, 30, 50 to another area can be knitted in a gradual fashion so as to provide smooth transitions between zones of compression. Gradual changes in compressive pressure in a garment 10, 30, 50 of the present invention avoids abrupt compression changes to a wearer, thereby reducing the risk of a tourniquet effect, impaired circulation, and/or skin breakdown. A zone of compressive pressure having a predetermined compressive pressure can be knit by using an elasticized yarn, for example, spandex yarn, having selected characteristics, such as denier, number of filaments, texturing, and covering with nylon. In embodiments, the selected spandex yarn can be fed into a knitting dial at a constant rate for a particular compressive pressure.

In the present invention, embodiments of a garment 10, 30, 50 can comprise a variety of yarns suitable for use in regular fashion socks as well as yarns usable in therapeutic compression garments. For example, in one embodiment, yarns of a sock 10, 50 comprise 66% nylon, 20% cotton, and 14% spandex. In an embodiment, spandex yarns have a denier of 560 and are double covered with 270/34 nylon. In other embodiments, a garment 10, 30, 50 can comprise 80% nylon and 20% spandex.

In embodiments, yarns utilized in garments of the present invention may include yarns have selected moisture management properties, for example, inner-facing hydrophobic yarn and outer-facing hydrophilic yarn.

Embodiments of garments 10, 30, 50 of the present invention can be made in various lengths, including ankle, knee, thigh, and waist lengths, for example. Embodiments of garments 10, 30, 50 of the present invention can be worn with or without a regular sock, including, for example, a running sock. While the illustrated embodiments depict lower extremity garments, in other embodiments, garments of the present invention can be made for and used on the upper extremities.

In a lower extremity garment of the present invention, such as garments 10, 30, 50, the heel area can have a different color than the remainder of the sock to help guide placement of the garment onto the foot and/or leg. In other embodiments, a garment can include colored yarns or alignment markings to aid in proper placement of the garment for achieving desired compressive pressures in particular anatomical areas.

Embodiments of a garment 10, 30, 50 of the present invention can provide increased compressive pressure and cushioning that may have therapeutic applications in selected areas of the underlying anatomical region(s). For example, such therapeutic compressive pressures may comprise compressive pressures in the 20-30 mm Hg range (Class I) and/or in the 30-40 mm Hg range (Class II) and/or in the 40-50 mm Hg range (Class III). In an illustrative embodiment, one area of a sock, such as the heel 12 and ball of the foot, as shown in FIGS. 1 and 2, may include compressive pressures in one range, while another area of the sock, such as the calf area 15, may include compressive pressures in the same or another range. In particular embodiments, such compressive pressures may be graduated along the length of a sock 10, 50 so as to enhance the flow in the venous and lymphatic systems.

Embodiments of the present invention can promote circulation and reduce impact stress in targeted areas of a wearer's foot and/or leg. Such features are particularly useful for athletes, who may experience increased pressure on specific parts of the foot and/or lower leg while participating in a particular sport. Such features are also useful for persons experiencing decreased foot and/or leg circulation and/or skin integrity in a specific area due to health conditions, for example, diabetes.

Embodiments of the present invention may be useful in the treatment of certain pathologic conditions. For example, it may be desirable to provide additional pressure on a venous stasis ulcer in a leg. Embodiments of a garment 10, 30, 50 having a denser, or more tightly knit, stitch pattern in a particular portion corresponding to the location of the venous ulcer can be used to provide increased compressive pressure to the ulcer area. In addition to providing increased cushioning over the ulcerated area, a more dense stitch pattern, such as a stitch pattern including tuck stitches, would help enhance circulation and promote healing in the affected area.

Embodiments of the present invention include methods for making a garment 10, 30, 50, for example, of the present invention. In one such embodiment, a first zone of compressive pressure is knit in a distal portion of a tubular garment 10, 30, 50. The first zone comprises a first stitch pattern that provides a first compressive pressure. A second zone of compressive pressure is knit in a proximal portion of the garment 10, 30, 50. The second zone comprises a second stitch pattern that provides a second compressive pressure. The first stitch pattern is more densely than at least a portion of the second stitch pattern, such that the first compressive pressure is greater than the second compressive pressure.

Such an embodiment may further include knitting the second zone of compressive pressure by knitting a first portion of the garment circumference comprising a first portion stitch pattern and a first portion compressive pressure. A second portion of the garment circumference is knit comprising a second portion stitch pattern and a second portion compressive pressure. The first portion stitch pattern is more densely knit than the second portion stitch pattern, such that the first portion compressive pressure is greater than the second portion compressive pressure. Knitting with a more densely knit stitch pattern can be accomplished in embodiments of the present invention by manipulating knitting needles on a circular knitting machine to various heights during the knitting cycle. For example, needles on the fourth yarn feed in a four feed machine can be held to the "tuck height" in order to knit tuck stitches. The needles can be held to knit tuck stitches in various patterns to provide varying degrees of compressive pressure in a particular garment circumference.

In another embodiment of a method, a plurality of zones of compressive pressure are knit. The plurality of zones of compressive pressure comprise decreasing amounts of compressive pressure from the distal portion to the proximal portion of the garment 10, 30, 50. In another embodiment, the first zone of compressive pressure can be knit with a smaller knitting circumference than the knitting circumference of the second zone of compressive pressure. This technique provides another means for increasing compressive pressure in a particular zone. In other embodiments, a garment, such as garments 10, 30, 50, can be knit utilizing a yarn in one zone of compressive pressure that is more elastic than yarn utilized in another zone of compressive pressure, such that the more elastic yarn provides another means for increasing compressive pressure in a particular zone. Knitting with a smaller knitting circumference and utilizing more elastic yarns can be used in combination with the "impact stitch," as described herein, to provide for increased compressive pressure in a particular circumferential zone.

Although the present invention has been described with reference to particular embodiments, it should be recognized that these embodiments are merely illustrative of the principles of the present invention. Those of ordinary skill in the art will appreciate that an impact protection and performance garment of the present invention may be constructed and implemented in other ways and embodiments. Accordingly, the description herein should not be read as limiting the present invention, as other embodiments also fall within the scope of the present invention.

What is claimed is:

1. A tubular garment, comprising:
a plurality of zones of compressive pressure about a circumference of the garment;
a first one of the zones of compressive pressure in a distal portion of the garment comprising a first stitch pattern that provides a first compressive pressure; and
a second one of the zones of compressive pressure in a proximal portion of the garment comprising a second stitch pattern that provides a second compressive pressure;
wherein the first stitch pattern is more dense than at least a portion of the second stitch pattern,
wherein the first compressive pressure is greater than the second compressive pressure,
wherein the second one of the zones of compressive pressure comprises (i) a first portion of the garment circumference comprising a first portion stitch pattern and a first portion compressive pressure and (ii) a second portion of the garment circumference comprising a second portion stitch pattern and a second portion compressive pressure,
wherein the first portion stitch pattern is more dense than the second portion stitch pattern, and
wherein the first portion compressive pressure is greater than the second portion compressive pressure.

2. The garment of claim 1, wherein the first portion stitch pattern and the second portion stitch pattern each comprise a cushioning stitch pattern.

3. The garment of claim 1, wherein the first portion stitch pattern and the second portion stitch pattern each comprise tuck stitches.

4. A tubular garment, comprising:
a plurality of zones of compressive pressure about a circumference of the garment;
a first one of the zones of compressive pressure in a distal portion of the garment comprising a first stitch pattern that provides a first compressive pressure; and
a second one of the zones of compressive pressure in a proximal portion of the garment comprising a second stitch pattern that provides a second compressive pressure;
wherein the first stitch pattern is more dense than at least a portion of the second stitch pattern,
wherein the first compressive pressure is greater than the second compressive pressure,
wherein each of the plurality of zones of compressive pressure comprises a knitting circumference, and
wherein the knitting circumference of the first one of the zones of compressive pressure is smaller than the knitting circumference of the second one of the zones of compressive pressure.

5. A tubular garment, comprising:
a plurality of zones of compressive pressure about a circumference of the garment;
a first one of the zones of compressive pressure in a distal portion of the garment comprising a first stitch pattern that provides a first compressive pressure; and
a second one of the zones of compressive pressure in a proximal portion of the garment comprising a second stitch pattern that provides a second compressive pressure;
wherein the first stitch pattern is more dense than at least a portion of the second stitch pattern,
wherein the first compressive pressure is greater than the second compressive pressure,
wherein each of the plurality of zones of compressive pressure comprises at least one yarn, and
wherein the at least one yarn of the first one of the zones of compressive pressure is more elastic than the at least one yarn of the second one of the zones of compressive pressure.

6. A tubular garment, comprising:
a plurality of zones of compressive pressure about a circumference of the garment;
a first one of the zones of compressive pressure in a distal portion of the garment comprising a first stitch pattern that provides a first compressive pressure; and
a second one of the zones of compressive pressure in a proximal portion of the garment comprising a second stitch pattern that provides a second compressive pressure;
wherein the first stitch pattern is more dense than at least a portion of the second stitch pattern,
wherein the first compressive pressure is greater than the second compressive pressure,
wherein the first stitch pattern comprises a four yarn feed pattern, and
wherein each stitch in a fourth yarn feed pattern comprises a tuck stitch.

7. The garment of claim 6, wherein the second stitch pattern comprises a four yarn feed pattern, wherein the at least a portion of the second stitch pattern comprises a fourth yarn feed pattern comprising a 1×1 rib stitch alternating with a tuck stitch.

8. The garment of claim 6, wherein the second stitch pattern comprises a four yarn feed pattern, wherein the at least a portion of the second stitch pattern comprises a fourth yarn feed pattern comprising a 1×1 alternate rib stitch alternating with a tuck stitch.

9. The garment of claim 6, wherein the second stitch pattern comprises a four yarn feed pattern, wherein the at least a portion of the second stitch pattern comprises a fourth yarn feed pattern comprising a 2×2 alternate rib stitch alternating with two tuck stitches.

10. The garment of claim 1,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 1×1 rib stitch alternating with a tuck stitch.

11. The garment of claim 1,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 1×1 alternate rib stitch alternating with a tuck stitch.

12. The garment of claim 1,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 2×2 alternate rib stitch alternating with two tuck stitches.

13. A tubular garment, comprising:
a zone of compressive pressure about a circumference of the garment;
a first portion of the garment circumference comprising a first portion stitch pattern and a first portion compressive pressure;
a second portion of the garment circumference comprising a second portion stitch pattern and a second portion compressive pressure,
wherein the first portion stitch pattern is more dense than the second portion stitch pattern,
wherein the first portion compressive pressure is greater than the second portion compressive pressure,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 1×1 rib stitch alternating with a tuck stitch.

14. A tubular garment, comprising:
a zone of compressive pressure about a circumference of the garment;
a first portion of the garment circumference comprising a first portion stitch pattern and a first portion compressive pressure;
a second portion of the garment circumference comprising a second portion stitch pattern and a second portion compressive pressure,
wherein the first portion stitch pattern is more dense than the second portion stitch pattern,
wherein the first portion compressive pressure is greater than the second portion compressive pressure,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 1×1 alternate rib stitch alternating with a tuck stitch.

15. A tubular garment, comprising:
a zone of compressive pressure about a circumference of the garment;
a first portion of the garment circumference comprising a first portion stitch pattern and a first portion compressive pressure;
a second portion of the garment circumference comprising a second portion stitch pattern and a second portion compressive pressure,
wherein the first portion stitch pattern is more dense than the second portion stitch pattern,
wherein the first portion compressive pressure is greater than the second portion compressive pressure,
wherein the first portion stitch pattern and the second portion stitch pattern each comprise a four yarn feed pattern,
wherein each stitch in a fourth yarn feed pattern of the first portion stitch pattern comprises a tuck stitch, and
wherein the second portion stitch pattern comprises a fourth yarn feed pattern comprising a 2×2 alternate rib stitch alternating with two tuck stitches.

16. A method of making a tubular garment, comprising:
knitting a first zone of compressive pressure in a distal portion of the garment, the first zone comprising a first stitch pattern that provides a first compressive pressure;
knitting a second zone of compressive pressure in a proximal portion of the garment, the second zone comprising a second stitch pattern that provides a second compressive pressure; and
knitting the first stitch pattern more densely than at least a portion of the second stitch pattern,
wherein the first compressive pressure is greater than the second compressive pressure,
wherein the knitting the second zone of compressive pressure comprises
  (i) knitting a first portion of the garment circumference comprising a first portion stitch pattern and a first portion compressive pressure, and
  (ii) knitting a second portion of the garment circumference comprising a second portion stitch pattern and a second portion compressive pressure,
wherein the first portion stitch pattern is more densely knit than the second portion stitch pattern, and
wherein the first portion compressive pressure is greater than the second portion compressive pressure.

17. A method of making a tubular garment, comprising:
knitting a first zone of compressive pressure in a distal portion of the garment, the first zone comprising a first stitch pattern that provides a first compressive pressure;
knitting a second zone of compressive pressure in a proximal portion of the garment, the second zone comprising a second stitch pattern that provides a second compressive pressure; and
knitting the first stitch pattern more densely than at least a portion of the second stitch pattern,
wherein the first compressive pressure is greater than the second compressive pressure,
wherein the knitting the first and second zones of compressive pressure further comprises knitting a plurality of zones of compressive pressure, and
wherein the plurality of zones of compressive pressure comprise decreasing amounts of compressive pressure from the distal portion to the proximal portion of the garment.

18. A method of making a tubular garment, comprising:
knitting a first zone of compressive pressure in a distal portion of the garment, the first zone comprising a first stitch pattern that provides a first compressive pressure;

knitting a second zone of compressive pressure in a proximal portion of the garment, the second zone comprising a second stitch pattern that provides a second compressive pressure; and knitting the first stitch pattern more densely than at least a portion of the second stitch pattern, wherein the first compressive pressure is greater than the second compressive pressure, wherein each of the first and second zones of compressive pressure comprises a knitting circumference, and wherein the knitting circumference of the first zone of compressive pressure is smaller than the knitting circumference of the second zone of compressive pressure.

19. A method of making a tubular garment, comprising:

knitting a first zone of compressive pressure in a distal portion of the garment, the first zone comprising a first stitch pattern that provides a first compressive pressure;

knitting a second zone of compressive pressure in a proximal portion of the garment, the second zone comprising a second stitch pattern that provides a second compressive pressure; and knitting the first stitch pattern more densely than at least a portion of the second stitch pattern, wherein the first compressive pressure is greater than the second compressive pressure, wherein the knitting the first and second zones of compressive pressure further comprises knitting a plurality of zones of compressive pressure, wherein each of the plurality of zones of compressive pressure comprises at least one yarn, and wherein the at least one yarn of the first zone of compressive pressure is more elastic than the at least one yarn of the second zone of compressive pressure.

20. A method of making a tubular garment comprising:

knitting a first zone of compressive pressure in a distal portion of the garment, the first zone comprising a first stitch pattern that provides a first compressive pressure;

knitting a second zone of compressive pressure in a proximal portion of the garment, the second zone comprising a second stitch pattern that provides a second compressive pressure; and knitting the first stitch pattern more densely than at least a portion of the second stitch pattern, wherein the first compressive pressure is greater than the second compressive pressure, wherein the first stitch pattern comprises a four yarn feed pattern, and wherein each stitch in a fourth yarn feed pattern comprises a tuck stitch.

21. The method of claim 16, wherein the first portion stitch pattern comprises a four yarn feed pattern, and wherein each stitch in a fourth yarn feed pattern of the first portion stitch pattern comprises a tuck stitch.

* * * * *